United States Patent [19]
Kemp et al.

[11] Patent Number: 5,688,760
[45] Date of Patent: Nov. 18, 1997

[54] POLYPEPTIDES HAVING BONE RESORPTION INHIBITORY ACTIVITY COMPRISING PTHRP-DERIVED SEQUENCES

[75] Inventors: Bruce E. Kemp, Kew; Geoffrey C. Nicholson, Geelong; Thomas J. Martin, Kew; Anna J. Fenton, Geelong, all of Australia; R. Glenn Hammonds, Berkeley, Calif.

[73] Assignees: Genentech, Inc., San Francisco, Calif.; The University of Melbourne, Victoria, Australia

[21] Appl. No.: 64,111

[22] PCT Filed: Dec. 13, 1991

[86] PCT No.: PCT/AU91/00580

§ 371 Date: Aug. 12, 1993

§ 102(e) Date: Aug. 12, 1993

[87] PCT Pub. No.: WO92/10511

PCT Pub. Date: Jun. 25, 1992

[30] Foreign Application Priority Data

Dec. 13, 1990 [AU] Australia .................................. PK3879
Nov. 19, 1991 [AU] Australia .................................. PK9567

[51] Int. Cl.[6] .......................... C07K 7/06; C07K 7/08; C07K 14/635; A61K 38/29
[52] U.S. Cl. .......................... 514/2; 514/8; 514/12; 514/13; 514/14; 514/15; 514/16; 514/17; 530/324; 530/325; 530/326; 530/327; 530/328; 530/329; 530/330; 530/350; 530/397; 530/399
[58] Field of Search .................... 530/324, 325, 530/326, 327, 328, 329, 330, 350, 399, 397; 514/2, 8, 12, 13, 14, 15, 16, 17; 435/69.1, 69.4, 172.3

[56] References Cited

U.S. PATENT DOCUMENTS 4,698,328 10/1987 Neer et al. .................... 514/12
5,312,810 5/1994 Wood et al. .................... 514/12

FOREIGN PATENT DOCUMENTS

19384/88 12/1987 Australia .
8809376 12/1988 WIPO .

OTHER PUBLICATIONS

Peninsula Laboratories, Inc. —Product availability notice, 1987.
Suva, et al. *Science* 237, 893 (1987).
Moseley, et al. *PNAS* 85, 5048 (1987).
Sone et al. 1992. Endocrinology 131:2742–6.
Whitfield et al. 1994. J. Cell. Physiol. 158:518–22.
Gagnon et al. 1993. J. Bone Min. Res. 8: 497–503.
Fenton et al. 1991. Endocrinology 129: 1762–8.
Fenton et al. 1991. Endocrinology 129:3424–6.
Kalu. 1991. Bone and Mineral 15: 175–92.
Bowie et al. 1987. Science 247: 1306–1310.
Barlet et al., "Synthetic parathyroid hormone–related peptide(1–34) fragment stimulates placental calcium transfer in ewes," *J. Endocrin.*, 127:33–37 (1990).
Martin, T.J., "Hormones in the Coupling of Bone Resorption and Formation," *Osteoporosis Int.*, 1:121–125 (1993).
Suda, T. et al., "Modulation of Osteoclast Differentiation," *Endocrine Reviews*, 13(1) 66–80 (1992).
Martin, T.J., et al., in "Handbook for Experimental Pharmacology," vol. 17, Physiology and Pharmacology of Bone, Mundy, G. and Martin, T.J. (eds.), Springer–Verlaag, Berlin, pp. 149–183 (1993).
Derwent Abstract Accession No. 90–294318/39, class B04, JP,A, 02–207099 (Tonen Corp.), 16 Aug. 1990.

*Primary Examiner*—Vasu S. Jagannathan
*Assistant Examiner*—Elizabeth C. Kemmerer
*Attorney, Agent, or Firm*—Walter H. Dreger

[57] ABSTRACT

Polypeptides comprising an N-terminal amino acid sequence corresponding to amino acids 107-111 of parathyroid hormone related protein (PTHrP) having bone resorption inhibitory activity are provided. The polypeptides are provided in pharmaceutical compositions for the treatment of diseases and disorders where inhibition of bone resorption is indicated.

19 Claims, 3 Drawing Sheets

| | | | | | | | | | | | |
|---|---|---|---|---|---|---|---|---|---|---|---|
| Met -36 | Gln | Arg | Arg | Leu | Val -30 | Gln | Trp | Ser | Val | Ala -25 | Val | Phe | Leu |

```
Met Gln Arg Arg Leu Val Gln Gln Trp Ser Val Ala Val Phe Leu
-36                      -30                     -25
Leu Ser Tyr Ala Val Pro Ser Cys Gly Arg Ser Val Glu Gly Leu
    -20             -15                     -10
Ser Arg Arg Leu Lys Arg Ala Val Ser Glu His Gln Leu Leu His
    - 5              1              5
Asp Lys Gly Lys Ser Ile Gln Asp Leu Arg Arg Arg Phe Phe Leu
 10              15                  20
His His Leu Ile Ala Glu Ile His Thr Ala Glu Ile Arg Ala Thr
 25              30                  35
Ser Glu Val Ser Pro Asn Ser Lys Pro Ser Pro Asn Thr Lys Asn
 40              45                  50
His Pro Val Arg Phe Gly Ser Asp Asp Glu Gly Arg Tyr Leu Thr
 55              60                  65
Gln Glu Thr Asn Lys Val Glu Thr Tyr Lys Glu Gln Pro Leu Lys
 70              75                  80
Thr Pro Gly Lys Lys Lys Gly Lys Pro Gly Lys Arg Lys Glu
 85              90                  95
Gln Glu Lys Lys Lys Arg Arg Thr Arg Ser Ala Trp Leu Asp Ser
100             105                 110
Gly Val Thr Gly Ser Gly Leu Glu Gly Asp His Leu Ser Asp Thr
115             120                 125
                              *          *
Ser Thr Thr Ser Leu Glu Leu Asp Ser Arg Arg His Leu Leu Trp
130             135                 140
Gly Leu Lys Lys Lys Lys Glu Asn Asn Arg Arg Thr His His Met
145             150                 155
                                              *
Gln Leu Met Ile Ser Leu Phe Lys Ser Pro Leu Leu Leu Leu
160             165                 170
```

FIG._1

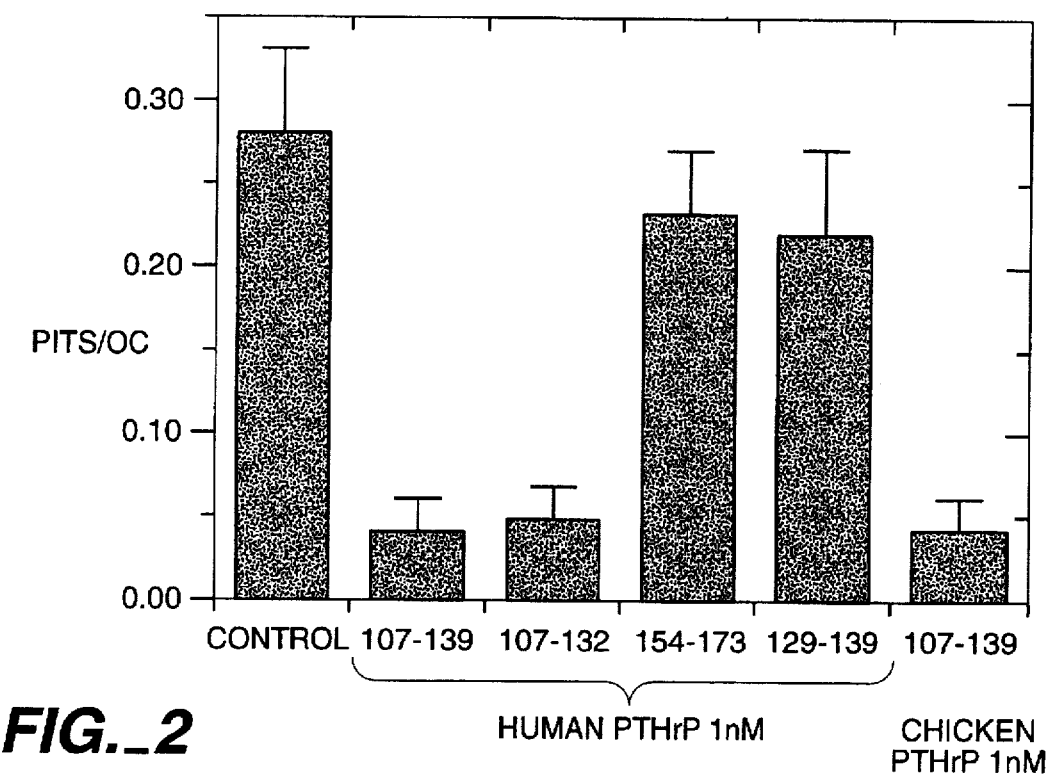
FIG._2
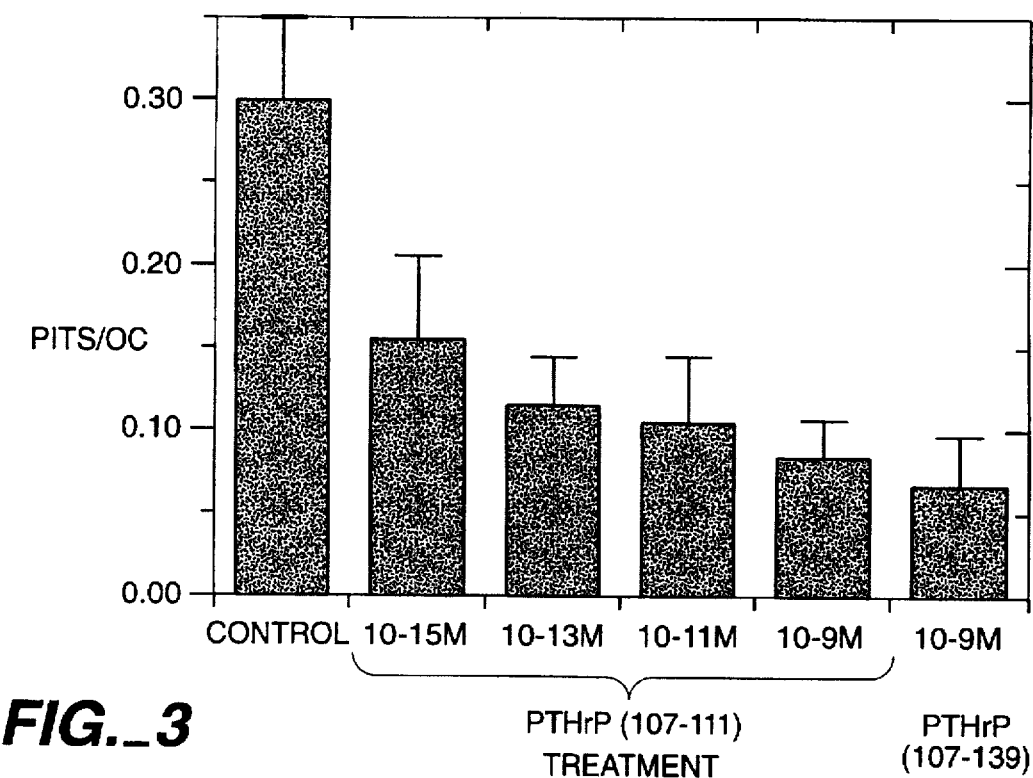
FIG._3

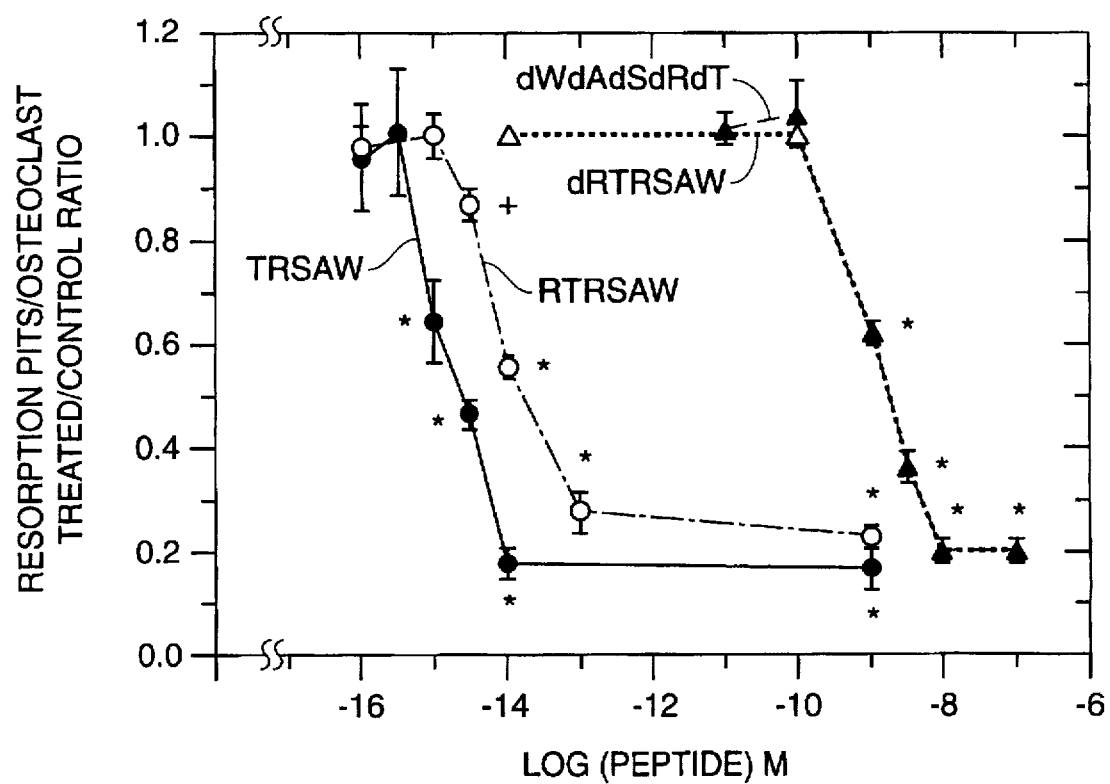
FIG._4

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
( A ) LENGTH: 209 amino acids (B) TYPE: amino acid
(C) STRANDEDNESS:
(D) TOPOLOGY: linear (ii) MOLECULE TYPE: peptide (xi) SEQUENCE DESCRIPTION: SEQ ID NO:1:

| Met -36 | Gln | Arg | Arg | Leu | Val -30 | Gln | Gln | Trp | Ser | Val -25 | Ala | Val | Phe | Leu | Leu |
| Ser -20 | Tyr | Ala | Val | Pro | Ser -15 | Cys | Gly | Arg | Ser | Val -10 | Glu | Gly | Leu | Ser | Arg -5 |
| Arg | Leu | Lys | Arg | Ala 1 | Val | Ser | Glu | His 5 | Gln | Leu | Leu | His | Asp 10 | Lys | Gly |
| Lys | Ser | Ile 15 | Gln | Asp | Leu | Arg | Arg 20 | Arg | Phe | Phe | Leu 25 | His | His | Leu | Ile |
| Ala | Glu 30 | Ile | His | Thr | Ala 35 | Glu | Ile | Arg | Ala | Thr 40 | Ser | Glu | Val | Ser | Pro |
| Asn 45 | Ser | Leu | Pro | Ser | Pro 50 | Asn | Thr | Lys | Asn | His 55 | Pro | Val | Arg | Phe | Gly 60 |
| Ser | Asp | Asp | Glu | Gly 65 | Arg | Tyr | Leu | Thr | Gln 70 | Glu | Thr | Asn | Lys | Val 75 | Glu |
| Thr | Tyr | Lys | Glu 80 | Gln | Pro | Leu | Lys | Thr 85 | Pro | Gly | Lys | Lys | Lys 90 | Lys | Gly |
| Lys | Pro | Gly 95 | Lys | Arg | Lys | Glu | Gln 100 | Glu | Lys | Lys | Arg | Arg 105 | Thr | Arg |
| Ser | Ala | Trp | Leu 110 | Asp | Ser | Gly | Val 115 | Thr | Gly | Ser | Gly 120 | Leu | Glu | Gly | Asp |
| His 125 | Leu | Ser | Asp | Thr | Ser 130 | Thr | Thr | Ser | Leu | Glu 135 | Leu | Asp | Ser | Arg | Arg 140 |
| His | Leu | Leu | Trp | Gly 145 | Leu | Lys | Lys | Lys | Lys 150 | Glu | Asn | Asn | Arg | Arg 155 | Thr |
| His | His | Met | Gln 160 | Leu | Met | Ile | Ser | Leu 165 | Phe | Lys | Ser | Pro | Leu 170 | Leu | Leu |

Leu (2) INFORMATION FOR SEQ ID NO:2:

(i) SEQUENCE CHARACTERISTICS:
(A) LENGTH: 33 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:2:

| Thr 1 | Arg | Ser | Ala | Trp 5 | Leu | Asp | Ser | Gly | Val 10 | Thr | Gly | Ser | Gly | Leu 15 | Glu |
| Gly | Asp | His | Leu 20 | Ser | Asp | Thr | Ser | Thr 25 | Thr | Ser | Leu | Glu | Leu 30 | Asp | Ser |

Arg (2) INFORMATION FOR SEQ ID NO:3:

(i) SEQUENCE CHARACTERISTICS:
(A) LENGTH: 5 amino acids
(B) TYPE: amino acid
(C) STRANDEDNESS:
(D) TOPOLOGY: linear (ii) MOLECULE TYPE: peptide ( x i ) SEQUENCE DESCRIPTION: SEQ ID NO:3:

Thr Arg Ser Ala Trp
1               5

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:4:

Arg Thr Arg Ser Ala Trp
1               5

( 2 ) INFORMATION FOR SEQ ID NO:5:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:5:

Pro Thr Arg Ser Ala Trp
1               5

( 2 ) INFORMATION FOR SEQ ID NO:6:

( i ) SEQUENCE CHARACTERISTICS:
        ( A ) LENGTH: 5 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 1

( x i ) SEQUENCE DESCRIPTION: SEQ ID NO:6:

Thr Arg Ser Ala Trp
1               5

( 2 ) INFORMATION FOR SEQ ID NO:7:

( i ) SEQUENCE CHARACTERISTICS:
        ( A ) LENGTH: 5 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:7:

Pro Arg Ser Ala Trp
1               5

( 2 ) INFORMATION FOR SEQ ID NO:8:

( i ) SEQUENCE CHARACTERISTICS:
        ( A ) LENGTH: 5 amino acids
        ( B ) TYPE: amino acid ( C ) STRANDEDNESS:
            ( D ) TOPOLOGY: linear ( i i ) MOLECULE TYPE: peptide ( x i ) SEQUENCE DESCRIPTION: SEQ ID NO:8:

Ala  Arg  Ser  Ala  Trp
    1                   5

( 2 ) INFORMATION FOR SEQ ID NO:9:

( i ) SEQUENCE CHARACTERISTICS:
            ( A ) LENGTH: 5 amino acids
            ( B ) TYPE: amino acid
            ( C ) STRANDEDNESS:
            ( D ) TOPOLOGY: linear ( i i ) MOLECULE TYPE: peptide ( x i ) SEQUENCE DESCRIPTION: SEQ ID NO:9:

Thr  Lys  Ser  Ala  Trp
    1                   5

( 2 ) INFORMATION FOR SEQ ID NO:10:

( i ) SEQUENCE CHARACTERISTICS:
            ( A ) LENGTH: 5 amino acids
            ( B ) TYPE: amino acid
            ( C ) STRANDEDNESS:
            ( D ) TOPOLOGY: linear ( i i ) MOLECULE TYPE: peptide ( x i ) SEQUENCE DESCRIPTION: SEQ ID NO:10:

Thr  Arg  Ala  Ala  Trp
    1                   5

( 2 ) INFORMATION FOR SEQ ID NO:11:

( i ) SEQUENCE CHARACTERISTICS:
            ( A ) LENGTH: 5 amino acids
            ( B ) TYPE: amino acid
            ( C ) STRANDEDNESS:
            ( D ) TOPOLOGY: linear ( i i ) MOLECULE TYPE: peptide ( x i ) SEQUENCE DESCRIPTION: SEQ ID NO:11:

Ala  Arg  Ala  Ala  Trp
    1                   5

( 2 ) INFORMATION FOR SEQ ID NO:12:

( i ) SEQUENCE CHARACTERISTICS:
            ( A ) LENGTH: 5 amino acids
            ( B ) TYPE: amino acid
            ( C ) STRANDEDNESS:
            ( D ) TOPOLOGY: linear ( i i ) MOLECULE TYPE: peptide ( i x ) FEATURE:
            ( A ) NAME/KEY: Modified-site
            ( B ) LOCATION: 4

( x i ) SEQUENCE DESCRIPTION: SEQ ID NO:12:

Thr  Arg  Ser  Ala  Trp
    1                   5

( 2 ) INFORMATION FOR SEQ ID NO:13:

( i ) SEQUENCE CHARACTERISTICS:
   ( A ) LENGTH: 5 amino acids
   ( B ) TYPE: amino acid
   ( C ) STRANDEDNESS:
   ( D ) TOPOLOGY: linear ( i i ) MOLECULE TYPE: peptide ( x i ) SEQUENCE DESCRIPTION: SEQ ID NO:13:

Thr Arg Ser Ala Tyr
1               5

( 2 ) INFORMATION FOR SEQ ID NO:14:

( i ) SEQUENCE CHARACTERISTICS:
      ( A ) LENGTH: 5 amino acids
      ( B ) TYPE: amino acid
      ( C ) STRANDEDNESS:
      ( D ) TOPOLOGY: linear ( i i ) MOLECULE TYPE: peptide ( i x ) FEATURE:
      ( A ) NAME/KEY: Modified-site
      ( B ) LOCATION: 5

( x i ) SEQUENCE DESCRIPTION: SEQ ID NO:14:

Thr Arg Ser Ala Gly
1               5

( 2 ) INFORMATION FOR SEQ ID NO:15:

( i ) SEQUENCE CHARACTERISTICS:
      ( A ) LENGTH: 9 amino acids
      ( B ) TYPE: amino acid
      ( C ) STRANDEDNESS:
      ( D ) TOPOLOGY: linear ( i i ) MOLECULE TYPE: peptide ( x i ) SEQUENCE DESCRIPTION: SEQ ID NO:15:

Thr Arg Cys Ala Trp Pro Gly Thr Cys
1               5

( 2 ) INFORMATION FOR SEQ ID NO:16:

( i ) SEQUENCE CHARACTERISTICS:
      ( A ) LENGTH: 5 amino acids
      ( B ) TYPE: amino acid
      ( C ) STRANDEDNESS:
      ( D ) TOPOLOGY: linear ( i i ) MOLECULE TYPE: peptide ( x i ) SEQUENCE DESCRIPTION: SEQ ID NO:16:

Thr His Ser Ala Trp
1               5

( 2 ) INFORMATION FOR SEQ ID NO:17:

( i ) SEQUENCE CHARACTERISTICS:
      ( A ) LENGTH: 4 amino acids
      ( B ) TYPE: amino acid
      ( C ) STRANDEDNESS:
      ( D ) TOPOLOGY: linear ( i i ) MOLECULE TYPE: peptide ( i x ) FEATURE:
      ( A ) NAME/KEY: Modified-site
      ( B ) LOCATION: 4

( x i ) SEQUENCE DESCRIPTION: SEQ ID NO:17:

Thr Arg Ser Ala
1

( 2 ) INFORMATION FOR SEQ ID NO:18:

( i ) SEQUENCE CHARACTERISTICS:
      ( A ) LENGTH: 5 amino acids
      ( B ) TYPE: amino acid
      ( C ) STRANDEDNESS:
      ( D ) TOPOLOGY: linear ( i i ) MOLECULE TYPE: peptide ( x i ) SEQUENCE DESCRIPTION: SEQ ID NO:18:

Ser Arg Thr Ala Trp
1                 5

( 2 ) INFORMATION FOR SEQ ID NO:19:

( i ) SEQUENCE CHARACTERISTICS:
      ( A ) LENGTH: 5 amino acids
      ( B ) TYPE: amino acid
      ( C ) STRANDEDNESS:
      ( D ) TOPOLOGY: linear ( i i ) MOLECULE TYPE: peptide ( i x ) FEATURE:
      ( A ) NAME/KEY: Modified-site
      ( B ) LOCATION: 1

( x i ) SEQUENCE DESCRIPTION: SEQ ID NO:19:

Ala Arg Ser Ala Trp
1                 5

( 2 ) INFORMATION FOR SEQ ID NO:20:

( i ) SEQUENCE CHARACTERISTICS:
      ( A ) LENGTH: 5 amino acids
      ( B ) TYPE: amino acid
      ( C ) STRANDEDNESS:
      ( D ) TOPOLOGY: linear ( i i ) MOLECULE TYPE: peptide ( i x ) FEATURE:
      ( A ) NAME/KEY: Modified-site
      ( B ) LOCATION: 5

( x i ) SEQUENCE DESCRIPTION: SEQ ID NO:20:

Thr Arg Ser Ala Ala
1                 5

( 2 ) INFORMATION FOR SEQ ID NO:21:

( i ) SEQUENCE CHARACTERISTICS:
      ( A ) LENGTH: 5 amino acids
      ( B ) TYPE: amino acid
      ( C ) STRANDEDNESS:
      ( D ) TOPOLOGY: linear ( i i ) MOLECULE TYPE: peptide ( i x ) FEATURE:
      ( A ) NAME/KEY: Modified-site
      ( B ) LOCATION: 1

( x i ) SEQUENCE DESCRIPTION: SEQ ID NO:21:

Thr Arg Ser Ala Trp (2) INFORMATION FOR SEQ ID NO:22:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:22:

Tyr Arg Ser Ala Trp
    1                5

(2) INFORMATION FOR SEQ ID NO:23:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:23:

Thr Ala Ser Ala Trp
    1                5

(2) INFORMATION FOR SEQ ID NO:24:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:24:

Thr Arg Ser Pro Trp
    1                5

(2) INFORMATION FOR SEQ ID NO:25:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 5

(xi) SEQUENCE DESCRIPTION: SEQ ID NO:25:

Thr Arg Ser Ala Phe
    1                5

(2) INFORMATION FOR SEQ ID NO:26:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide ( x i ) SEQUENCE DESCRIPTION: SEQ ID NO:26:

Trp Ala Ser Arg Thr
1               5

POLYPEPTIDES HAVING BONE RESORPTION INHIBITORY ACTIVITY COMPRISING PTHRP-DERIVED SEQUENCES

This invention relates to compounds and compositions which inhibit bone resorption, and to methods for inhibiting bone resorption. In particular, this invention is concerned with carboxyl terminal fragments of the polypeptide PTHrP (Parathyroid Hormone Related Protein) and derivatives thereof which inhibit bone resorption.

PTHrP (also known by the name Adenylate Cyclase Stimulating Factor—ACSF) is a protein which was first isolated and purified to homogeneity by Prof. T. J. Martin and colleagues from a squamous carcinoma (BEN cells) cell extract (Moseley et al., Proc. Natl. Acad. Sci. 85: 5048–5052, 1987). Nucleic acid encoding PTHrP was isolated and characterised by Suva et al. (Science 237: 893–896, 1987). The PTHrP gene encodes a polypeptide with a 31 residue signal sequence followed by a 5 residue basic Pro sequence and then the sequence of PTHrP. The human gene transcript can undergo alternative splicing to generate mature PTHrP comprising amino acids 1-139, 1-141 or 1-173. It is believed that the 1-141 form may predominate. The amino acid sequence of prepro PTHrP (SEQ ID NO:1) is depicted in FIG. 1, which shows the various splice variants (designated with an *).

PTHrP contains three principle domains. The N-terminal domain, extending from about residue 1 to residue 83 and termed the N-terminal domain, contains sequence which is related to PTH and contains the PTH receptor binding functionality of PTHrP. Thereafter in the C-terminal direction lies a highly basic region extending about from residues 84 to 106, termed the basic peptide, and finally the C-terminal peptide at about residues 107 to 141 or (107-139 or 107-173 in other splice variants).

The actions of PTHrP resemble closely those of PTH (parathyroid hormone) including activation of adenylate cyclase, simulation of bone resorption in organ culture by isolated osteoclasts in-vitro, and, promotion of phosphate excretion and kidney formation of cyclic AMP in-vivo. The PTHrP polypeptide is associated with non-metastic bone destruction and hypercalcemia, which result from excessive bone resorption.

Excessive bone resorption is associated with a number of non-malignant and malignant diseases, such as osteoporosis, Paget's disease of bone, humoral hypercalcemia of malignancy and metestic bone disease. In addition, astronauts experience increased bone resorption under conditions of zero gravity. Excessive bone resorption leads to brittle and weak bones which become increasingly susceptible to fracture and breakage, and deformation under body weight which may give rise to bone curvature and associated posture problems.

Hypercalcemia may also be associated with the calcification of organs and tissues, that is, the deposition of calcium within tissues and organs. Calcification may lead to impairment of organ function, and cell death. The kidneys are parcicularly susceptible to calcification, leading to reduced function and ultimately kidney failure with attendant serious complications.

It has now been discovered that carboxyl terminal fragments of PTHrP comprising at least amino acids 107-111 (that is, amino acids 107-111 through 107-173) and derivatives thereof are potent inhibitors of bone resorption. This surprising observation is in distinct contrast to the primary activity of "whole" PTHrP and N-terminal fragments thereof which promote bone resorption. This invention is predicated on this surprising discovery.

In accordance with a first aspect of this invention, there is provided a compound having bone resorption inhibitory activity which comprises a carboxyl terminal fragment of PTHrP consisting of at least amino acids 107-111 of PTHrP, or a derivative thereof, with the proviso that PTHrP 107-138 is specifically excluded.

The compounds in accordance with this aspect of the invention thus include any carboxyl terminal fragment of PTHrP from amino acids 107-111, through to amino acid 107-173, that is peptides comprising between 5 and 66 amino acids, and derivatives thereof. Such compounds include, for example, PTHrP(107-111), PTHrP(107-112), PTHrP(107-119), PTHrP(107-132), PTHrP(107-150) and PTHrP(107-173). As all of such fragments comprise amino acids 107-111 of PTHrP they will contain bone resorption inhibitory activity.

The amino terminus of amino acid 107 of PTHrP may be protected with a hydrolysable protecting group. The term "hydrolysable protecting group" is used herein in its broadest sense to refer to any group which is hydrolysable (such as by acid hydrolysis, base hydrolysis, enzymic hydrolysis by proteolytic or other enzymes and the like) to give a free N-terminus. Amino protecting groups are well known in the art, and are described for example in Green et al. (1981, Protective Groups in Organic Synthesis, John Wiley & Sons, Inc., which is incorporated herein by reference). Examples of hydrolysable protecting groups include acyl, particularly organic acyl, for example, substituted or unsubstituted aliphatic hydrocarbon-oxycarbonyl such as alkoxycarbonyl (e.g. methoxycarbonyl, ethoxycarbonyl, propoxycarbonyl, butoxycarbonyl, t-butoxycarbonyl, 5-pentoxycarbonyl), haloalkoxycarbonyl (e.g. chloromethoxycarbonyl, tribromoethoxycarbonyl, trichloroethoxycarbonyl), an alkane- or arene-sulfonylalkoxycarbonyl (e.g. 2-(mesyl) ethoxycarbonyl, 2-(p-toluanesulonyl)ethoxycarbonyl), an alkylthio- or arylthioalkoxycarbonyl (e.g. 2-(ethylthio) ethoxycarbonyl, 2-(p-tolylthio)ethoxycarbonyl), substituted or unsubstituted alkanoyl such as, halo(lower) alkanoyl (e.g. formyl, trifluoroacetyl), a monocyclic or fused cyclic-alicyclic oxycarbonyl (e.g. cyclohexyloxycarbonyl, adamantyloxycarbonyl, isobornyloxycarbonyl), substituted or unsubstituted alkenyloxycarbonyl (e.g. allyoxycarbonyl), substituted or unsubstituted alkynyloxycarbonyl (e.g. 1,1-dimethylpropargyloxycarbonyl), substituted or unsubstituted aryloxycarbonyl (e.g. phenoxycarbonyl, p-methylphenoxycarbonyl), substituted or unsubstituted aralkyloxycarbonyl (e.g. benzyloxycarbonyl, p-nitrobenzyloxycarbonyl, p-phenylazobenzyloxycarbonyl, p-(p-methoxyphenylazo)-benzyloxycarbonyl, p-chlorobenzyloxycarbonyl, p-bromobenzyloxycarbonyl, α-naphthylmethoxycarbonyl, p-biphenylisopropoxycarbonyl, fluorenymethoxycarbonyl), substituted or unsubstituted arenesulfonyl (e.g. benzenesulfonyl, p-toluenesulfonyl), substituted or unsubstituted dialkylphosphoryl (e.g. dimethylphosphoryl), substituted or unsubstituted diaralkylphosphoryl (e.g. O,O-dibenzylphosphoryl), substituted or unsubstituted aryloxyalkanoyl (e.g. phenoxyacetyl, p-chlorophenoxyacetyl, 2-nitrophenoxyacetyl, 2-methyl-2-(2-nitro-phenoxy) propyonyl)

substituted or unsubstituted aryl such as phenyl, tolyl;
substituted or unsubstituted aralkyl such as benzyl, diphenylmethyl, trityl or nitrobenzyl or one or more amino acids. In relation to amino acid protecting groups, amino acid 106 of PTHrP is cleavable from the carboxy terminal fragment of PTHrP by proteolysis to yield a free N-terminus of amino acid 107. Where the compounds of this invention include PTHrP amino acid 106, it is to be understood that $[F_{110}; W_{117}; D_{122}; A_{133}$ or $E_{141}]$ PTHrP 106-141 is specifically excluded. As is apparent from the above, any amino acid protecting group which is hydrolysable, particularly under conditions in the human body, such as in the blood stream or digestive tract may be utilised in this invention.

Amino acids 107-111 of PTHrP are surprisingly plastic in that significant variation in amino acid sequence is tolerated without loss of bone resorption inhibitory activity. Derivatives of the compounds of this invention may be represented by the formulas (I) and (II) as set forth below:

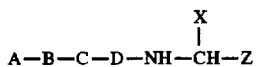

$$A-B-C-D-NH-CH-Z \quad \text{(I)}$$
(with X above CH)

wherein:
- A is a residue of any amino acid preferably Thr, Ala or Cys having a free N-terminus or an N-terminus protected with a hydrolysable protecting group;
- B is a basic residue of an amino acid, preferably, Arg or homoArg, optionally substituted at one or more methylene groups with halogen, $C_{1-3}$ alkyl and/or $C_{1-3}$ alkoxy;
- C is a non-polar or uncharged polar residue of an amino acid, preferably, Se, Ale, Thr or Cys, where hydroxyl or sulphydryl groups are optionally esterified or etherified to give physiologically hydrolysable esters or ethers;
- D is a non-polar or uncharged polar residue of an amino acid, preferably, Ale, Gly, amino isobutyric acid, Met, Ser, Thr or Cys optionally esterified or etherified with a physiologically hydrolysable ester or ether;
- X is the side chain of an aromatic amino acid, preferably, Tyr, Phe, methyl phenyl alanine, or napthyl alanine, where the phenyl ring of any such amino acid is optionally substituted with halogen, $NO_2$, $NH_2$, OH, $C_{1-3}$ alkyl and/or $C_{1-3}$ alkoxy; and Z is:
- $COOR_1$ where $R_1$ is H or $C_{1-3}$ lower alky;
- $(AA)(AA)_n$ where AA is any amino acid, n is an integer from 0 to 40, wherein if n is greater than 1, AA may be the same or different, and preferably at least one of AA is Cys to facilitate the incorporation of disulphide bonds which may stabilise the molecule;
- $CH_2OR_2$ where $R_2$ is hydrogen or the residue of a physiologically acceptable, physiologically hydrolysable ester or ether;

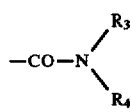

$$-CO-N\begin{matrix}R_3\\R_4\end{matrix}$$

wherein:
- $R_3$ is hydrogen, $C_{1-3}$ alkyl, phenyl, benzyl or $C_{9-10}$ phenylalkyl,
- $R_4$ is hydrogen, $C_{1-3}$ alkyl or, when $R_3$ is hydrogen or methyl, also a group of formula —$CH(R_5)$-U wherein
- $R_5$ is hydrogen, —$(CH_2)_2$—OH or —$(CH_2)_3$—OH, or represents the substituent attaching to the α-carbon atom of a natural α-amino acid; and U is a group of formula —$COOR_1$,

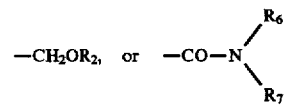

$$-CH_2OR_2, \text{ or } -CO-N\begin{matrix}R_6\\R_7\end{matrix}$$

wherein:
- $R_1$ and $R_2$ have the meanings given-above;
- $R_6$ is hydrogen or $C_{1-3}$ alkyl and
- $R_7$ is hydrogen, $C_{1-3}$ alkyl, phenyl or $C_{7-10}$ phenylalkyl, the group —$CH(R_5)$—X having the D- or L-configuration;
- with the proviso that PTHrP 107-138 is specifically excluded; and that where A is Ser, C is not Thr.

Compounds of the formula (II) have the formula:

$$_DW_DA_DS_DR_DT \quad \text{(II)}$$

wherein the various designations W, A, S, R, and T represent amino acids using the standard one letter code and $_D$ refers to the D-amino acid configuration.

Basic, non-polar and uncharged polar residues are well known in the art, and describe for example in Lehninger (Biochemistry, 2nd Edition, Worth Publishers Inc. 1978, which is incorporated herein by reference).

Amino acids of the formula (I) may be in the D- or L-configuration with the proviso that the resulting peptides have bone resorption inhibitory activity, which activity can be readily tested by routine bioassays as described herein. Peptides may contain amino acids in the D- or L-configuration or a combination thereof. Preferably compounds of the formula (I) are in the L-configuration.

As previously mentioned, applicants have found that a free N-terminus at amino acid 107 is generally necessary for bone resorption inhibitory activity. However, compounds of this invention which contain an N-terminal hydrolysable protecting group also possess bone resorption inhibitory activity where the protecting group is cleaved, such as in the digestive tract or blood stream of an animal.

In contrast, the nature of the carboxyl-terminal functionality of compounds of this invention is not of importance, as long as the compounds possess bone resorption inhibitory activity. Generally, carboxyl-terminal functionalities would be selected to increase peptide uptake, potency or stability. In this regard, physiologically hydrolysable esters or ethers, for example containing $C_{1-5}$ alkyl groupings, may increase peptide uptake and/or stability.

The term "carboxyl terminal fragments of PTHrP" as used herein refers to amino acids 107-111 of PTHrP through amino acids 107-173. These carboxyl terminal fragments may also be known as osteostatin.

Compounds comprising amino acids 107-111 and derivatives thereof, of the formulae (I) and (II) as set forth above, are particularly advantageous as they are more analogous to conventional pharmaceutical reagents in properties such as molecular weight, physiochemical properties and ease of synthesis than larger carboxyl terminal fragments of PTHrP and derivatives thereof.

Low molecular weight peptides, and the synthesis thereof are particularly amenable to standard solid phase (Kent, S. B. H., Ann. Rev. Biochem [1988] 57, 957–989) or liquid phase protein synthetic techniques (Finn, F. M., and Holmann, K., The Proteins, Edit Neurath, H., Hill, R. L., and Boeder, C. L., [1976] Academic Press New York. pp. 106–256), which are well known in the art of peptide chemistry. Peptides are produced by sequentially linking together by an amide bond two amino acids or peptide units (containing at least one amino acid) in protected or unprotected form. The synthetic peptides are characterized using techniques well known in the art, such as amino acid analysis, reverse phase HPLC and capillary electrophoresis.

Amino acids or derivatives thereof are therefore assembled into a peptide chain to give compounds of the formula (I). Peptide synthesis may take place on a solid support or in solution phase, whereafter the resultant peptide is treated with appropriate reagents to remove protecting groups, cleaved from a solid phase, and thereafter purified by standard techniques based on molecular weight (size exclusion chromatography), charge (cationic and anionic exchange), hydrophobicity, and the like. Peptides will generally be provided in homogenous form, or will be essentially pure, that is, comprise at least 90% by weight and preferably 95% or more of the desired peptide.

By way of example only, carboxyl terminal fragments of PTHrP may be prepared according to Fmoc or t-Boc chemistries (Kent, Supra), or other protein synthetic methodologies which are well known in the art.

PTHrP carboxyl terminal fragments and derivatives thereof may be made in recombinant cell culture, particularly where the fragments comprise around 15 amino acids or more. In order to do so, it is first necessary to secure nucleic acid encoding the particular PTHrP C-terminal fragment. This may be affected by nucleotide synthesis according to standard synthetic methods or by manipulation of human cDNA encoding PTHrP, as described by Suva et al. (Supra). Once the appropriate DNA fragment has been prepared, it is a straight-forward matter for those skilled in the art to insert PTHrP encoding nucleic acid into a replicable vector for further cloning or expression. Vectors are useful for performing two functions in collaboration with compatible host cells (a host-vector system). One function is to facilitate the cloning of the nucleic acid that encodes carboxy terminal fragments of PTHrP, i.e., to produce useable quantities of the nucleic acid. The other function is to direct expression of carboxy terminal fragments of PTHrP. One or both of these functions may be performed by the vector-host system.

Expression and cloning vectors, and host cells which may be used for the expression of carboxy terminal fragments of PTHrP are well known to persons skilled in the art and are described, for example, by Maniatis et al. (Molecular Cloning, A Laboratory Manual, Cold Spring Harbor Laboratory, 1982).

Expression and cloning vectors contain a nucleotide sequence which enables the vector to replicate in one or more selected host cells. Such sequences are well known for a variety of bacteria and in viruses.

Expression and cloning vectors should contain a selection gene, also known as a selectable marker for identification of vector containing cells. Such a gene generally encodes a protein product necessary for survival or growth of a host cell transformed with the vector. Selectable markers are well known in the art.

Expression vectors, unlike other cloning vectors, should contain a promoter which is recognised by the host organism and operably linked to the nucleic acid encoding PTHrP carboxy terminal fragments. PTHrP carboxy terminal fragments may be expressed in prokaryotic or eukaryotic cells, such as bacteria, yeast, insect, plant, animal, human or nucleated cells from other multi cellular organisms.

Carboxy terminal fragments of PTHrP are preferably recovered from cell culture as secreted proteins although they may be recovered from host cell lysates when directly expressed without a secretory sequence. The secreted or recovered product may be purified by well known protein purification steps such as gel filtration, ion-exchange chromatography and the like.

As low molecular weight peptides corresponding to the carboxyl terminus of PTHrP, such as PTHrP (107-111) and compounds of the formula (I), are particularly preferred, peptide synthetic techniques rather than recombinant methodologies will generally be employed.

Carboxyl terminal fragments of PTHrP comprising amino acids 107-111 and additional amino acids of PTHrP from 112 up to 173 may also be subject to variation, particularly in the region of amino acids 112-173 which do not themselves contribute to bone resorption inhibitory activity. Accordingly PTHrP amino acids 112 up to 173 may be subject to variations well known in the art, such as substitutions, deletions, insertions or modifications of amino acids with the proviso that such variants possess bone resorption inhibitory activity.

Commonly, derivatives will be substitutional variants, those in which at least one residue in the carboxy terminal fragment of PTHrP has been deleted and another residue inserted in its place. Substitutions are typically made in accordance with the following table:

TABLE 1

| Original Residue | Exemplary Substitutions |
| --- | --- |
| Ala | gly; ser |
| Arg | lys |
| Asn | Gln; his |
| Asp | glu |
| Cys | ser; ala |
| Gln | asn |
| Glu | asp |
| Gly | ala |
| His | asn; gln |
| Ile | leu; val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Insertions are introduced adjacent to selected residues at either the N- or C-terminal bonds and are preferably introduced in pairs.

Most substitutions and insertions will not produce radical changes in the characteristics of the PTHrP carboxy terminal fragments. Substitutional and insertional variants of carboxyl terminal fragment of PTHrP which may be employed in the present invention possess bone resorption inhibitory activity.

The amino acid sequence variants of this invention are preferably constructed by mutating the DNA sequence that encodes wild-type amino acid sequence. Generally, particular regions or sites of the DNA will be targeted for mutagenesis, and thus the general methodology employed to accomplish this is termed site-directed mutagenesis. The mutations are made using DNA modifying enzymes such as restriction endonucleases (which cleave DNA at particular locations), nucleases (which degrade DNA) and/or polymerases (which synthesise DNA).

Restriction endonuclease digestion of DNA followed by ligation may be used to generate deletions, as described in section 15.3 of Sambrook et al. (Molecular Cloning: A Laboratory Manual, second edition, Cold Spring Harbor Laboratory Press, New York [1989]). To use this method, it is preferable that the foreign DNA be inserted into a plasmid vector. A restriction map of both the foregin (inserted) DNA and the vector DNA must be available, or the sequence of the foreign DNA and the vector DNA must be known. The foreign DNA must have unique restriction sites that are not present in the vector. Deletions are then made in the foreign DNA by digesting it between these unique restriction sites, using the appropriate restriction endoucleases under conditions suggested by the manufacturer of the enzymes. If the restriction enzymes used create blunt ends or compatible, the ends can be directly ligated together using a ligase such as bacteriophage T4 DNA ligase and incubating the mixture at 16° C. for 1–4 hours in the presence of ATP and ligase buffer as described in section 1.68 of Sambrook et al., Supra. If the ends are not compatible, they must first be made blunt by using the Klenow fragment of DNA polymerase I or bacteriophage T4 DNA polymerase, both of which require the four deoxyribonucleotide triphosphates to fill-in the overhanging single-stranded ends of the digested DNA. Alternatively, the ends may be blunted using a nuclease such as nuclease S1 or mung-bean nuclease, both of which function by cutting back the overhanging single strands of DNA. The DNA is then religated using a ligase. The resulting molecule is a deletion variant.

A similar strategy may be used to construct insertion variants, as described in section 15.3 of Sambrook et al., Supra.. After digestion of the foreign DNA at the unique restriction site(s), an oligonucleotide is ligated into the site where the foreign DNA has been cut. The oligonucleotide is designed to code for the desired amino acids to be inserted and additionally has 5' and 3' ends that are compatible with the ends of the foreign DNA that have been digested, such that direct ligation is possible.

Oligonucleotide-directed mutagenesis is the preferred method for preparing the substitution variants of this invention. It may also be used to conveniently prepare deletion and insertion variants. This technique is well known in the art as described by Adelman et al., (DNA, 2: 183 [1983]).

Mutants with more than one amino acids substituted may be generated in one of several ways. If the amino acids are located close together in the polypeptide chain, they may be mutated simultaneously using one oligonucleotide that codes for all of the desired amino acid substitutions. If however, the amino acids are located some distance from each other (separated by more than ten amino acids, for example) it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. The alternative method involves two or more rounds of mutagenesis to produce the desired mutant. The first round is as described for the single mutants. The second round of mutagenesis utilises the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

Derivatives of carboxyl terminal fragments of PTHrP amino acids 107-111 through 107-173 and compounds of the formula (I) and (II) may also be produced by reacting targeted amino acid residues of a fragment of interest with an organic or other derivatizing agent which is capable of combining with selected side chains, terminal residues, or functional groups, or by harnessing mechanisms or post translational modifications functioning in selected recombinant host cells.

Cysteinyl residues most commonly are reacted with α-haloacetates (and corresponding amines), such as iodoacetic acid or iodoacetamide to give carboxymethyl or carboxyamidomethyl derivatives. Cysteinyl residues also are derivertized by reaction with bromotrifluoroacetone, α-bromo-β-(5-imidozoyl)propionic acid, chloroacetol phosphate, N-alkylmaleimides, 3-nitro-2-pyridyl disulfide, methyl 2-pyridyl disulfide, p-chloromercuribenzoate, 2-chloromercuri-4-nitrophenol or chloro-7-nitrobenzo-2-oxa-1,3-diazole. Since authentic PTHrP is largely devoid of cystsine residues, organic derivatization would be applicable only by insertional or substitutional cysteine-containing PTHrP carboxy terminal variants, for example PTHrP carboxy terminal fragments in which an N or C-terminal cysteine has been inserted in order to facilitate cross-linking to an immunogenic peptide.

Histidyl residues preferably are derivatized by reaction with diethylpyrocarbonte at pH 5.5 to 7.0 because this agent is relatively specific for histidyl side chains. Para-bromophenacyl bromide also is useful; the reaction should be performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α amino-containing residues include imidoesters such as methyl picolinimidate; pyridoxal phosphate; pyridoxal; borohydrides; trinitrobenzenesulfonic acid; O-methylisourea; 2,4-pentanedione; and transaminasecatalyzed reaction with glyoxylate.

Arginyl residues are modified by reaction with one of several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the ε-amino group of lysine as well as the arginine ω-amino group.

The specific modification of tyrosyl residues per se has been extensively studied, with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively. Tyrosyl residues are iodinated using $^{125}I$ or $^{131}I$ to prepare labelled proteins for use in radioimmunoassay, the chloramine T method being widely adopted per se for this purpose.

Carboxyl side groups (aspartyl or glutamyl) are selectively modified by reaction with carbodiimides (R'—N=C=N—R') such as 1-cyclohexyl-3-(2-morpholinyl-(4)-ethyl)carbodiimide or 1-ethyl-3-(4-azonia-4,4-dimethylpentyl)-carbodiimide. Furthermore; aspartyl and glutamyl residues are converted to asparaginyl and glutaminyl residues by reaction with ammonium ions, this being an alternative to mutating the nucleic acid to encode asparagine and glutamine.

Derivatization with bifunctional agents is useful for preparing intermolecular aggregates of proteins with immunogenic polypeptides as well as for cross-linking the carboxyl terminal fragments to a water insoluble support matrix or surface for use in assays or affinity purification of antibodies. Commonly used cross-linking agents include 1,1-bis (diazoacetyl)-2-phenylethane, glutaraldehyde, N-hydroxysuccinimide esters, for example esters with 4-azidosalicyclic acid, homobifunctional imidoesters including disuccinimidyl esters such as 3,3'-dithiobis (succinimidyl-propionate), and bifunctional maleimides such as bis-N-maleimido-1,8-octane. Derivatizing agents such as methyl-3-[(p-azido-phenyl)dithio]propioimidate yield photactivatable intermediates which are capable of forming cross-links in the presence of light. Alternatively, reactive water insoluble matrices such as cyanogen bromide activated carbohydrates and the reactive substrates described in U.S. Pat. Nos. 3,969,287; 3,691,016; 4,195,128; 4,247,642; 4,229,537 and 4,330,440 are employed for protein immobilisation.

Where compounds of this invention are produced recombinantly, certain post-translational derivatizations resulting from the action of recombinant host cells on the expressed polypeptide may arise. By "recombinant host cells" is meant prokaryotic or eukaryotic cells such as E. coli, various types of yeast cells, CHO cells and the like which contain expression vectors which express carboxyl terminal fragments of ACSF. Glutaminyl and asparaginyl residues may be post-transitionally deamidated to the corresponding glutamyl and aspartyl residues. Alternatively, these residues are deamidated under mildly acidic conditions. Either form of these residues falls within the scope herein.

Other post-translational modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W. H. Freeman & Co., San Francisco pp 79–86 [1983]), acetylation of the N-terminal amine and, in some instances, amidation of the C-terminal carboxyl.

The activity of carboxy terminal variants or derivatives of PTHrP can be readily evaluated by routine screening assays, to determine whether or not variants or derivatives possess bone resorption inhibitory activity. For example, osteoclasts may be settled on sections of bone and incubated in the presence of, and in the absence of test compounds. Osteoclasts can be determined histochemically and can then be removed following incubation with bone sections by, for example, ultrasonification and the bone surface examined by microscopy to measure resorption pits produced per isolated osteoclasts. The number of resorption pits may be counted and their areas quantitated, for example by digitized morphometry. The variants or derivatives with inhibitory activity on bone resorption will, of course, inhibit the activity of osteoclasts in resorption of bone, which can be readily ascertained by analysis of bone sections. Likewise, variants or derivatives which have no effect in inhibiting bone resorption or which stimulate bone resorption will be evidenced by the formation of resorption pits on bone-sections.

Other convenient assays may also be employed to detect activity of variants and derivatives of PTHrP carboxy terminal fragments.

Carboxyl terminal fragments of PTHrP and derivatives thereof may be prepared as non-toxic salts with such ions as sodium, potassium, phosphate, chloride and the like. Generally, PTHrP carboxyl terminal fragments are stored in phosphate buffered saline or may be lyophilized in the presence of an excipient including sugar alcohols, e.g. mannitol or sorbitol; monosaccharides, e.g., glucose, manuose, galactose or fructose; oligosuccharides such as maltrose, lactose or sucrose; and proteins such as human serum albumin.

The foregoing excipients also may contribute to the stablilty of PTHrP carboxy terminal fragments and derivatives to inactivation or precipitation upon aqueous storage, and may be-used together with other stabilizers which are conventional per se. Such stabilizers include chelating agents, e.g. EDTA; acidic amino acids; and nonionic surfactants such as polyethylene glycol or block copolymers of polyethylene and polypropylene glycol.

The carrier for infusion or injection of PTHrP carboxy terminal fragments may be a sterile isotonic aqueous solution, for example saline for injection or 5% dextrose. These preparations are injected or infused by intranasal, subcutaneous, intravenous, intraperitoneal or other conventional routes of administration.

PTHrP carboxyl terminal fragments and derivatives thereof may also be provided in a sustained release carrier. Suitable examples include semipermeable polymer matrices in the form of shaped articles, e.g. suppositories, or microcapsules. Implantable sustained release matrices include copolymers of L-glutamic acid and gamma ethyl-L-glutamate (U. Sidman et al., 1983, "Biopolymers" 22(1): 547–556), poly(2-hydroxyethylmethacrylate) (R. Langer et al., 1981, "J. Biomed. Mater. Res." 15:167–277 and R. Langer, 1982, "Chem. Tech." 12: 98–105), ethylene vinyl acetate (R. Langer et al., Id.), or poly-D-(−)-3-Hydroxybutyric acid (EP 133,988A). Sustained release compositions also include liposomally entrapped PTHrP carboxy terminal fragments. Liposomes containing PTHrP carboxy terminal fragments are prepared by methods known per se: DE 3,219,121A; Epstein et al., 1985, "Proc. Natl. Acad. Sci. U.S.A." 82: 3688–3692; Hwang et al., 1980, "Proc. Natl. Acad. Sci, U.S.A." 77: 4030–4034; EP 52322A; EP 36676A; EP 88046A; EP 143949A; EP 142641A; Japanese Patent Application 83-118008; U.S. Pat Nos. 4,485,045 and 4,544,545; and EP 102,324A. Ordinarily the liposomes are of the small (about 200–800 Angstroms) unilamelar type in which the lipid content is greater than about 30 mol. % cholesterol, the selected proportion being adjusted for the optimal rate of PTHrP carboxy terminal fragment leakage.

In accordance with another aspect of this invention there is provided a composition comprising at least amino acids 107-111 of the carboxyl terminus of PTHrP or a derivative thereof as herein described, in association with one or more pharmaceutically acceptable carriers or excipients.

In another aspect of this invention, there is provided a chimeric molecule which comprises at least amino acids 107-111 of the carboxyl terminus of PTHrP or a derivative thereof chemically conjugated for example by disulphide, ether or amido linkage, or expressed as a fusion product, or otherwise associated by electrostatic, hydrophobic, or other like interaction with a compound having cytotoxic activity, targeting activity (that is affinity for particular cell types) or bone resorption inhibition activity. Suitable compounds include antibodies which bind to various cell types; cytotoxic molecules such as the A-chain of ricin and cytotoxic drugs; and compounds having bone resorption inhibitory activity such as calcitonin.

In yet another aspect of this invention, there is provided a method for the inhibition of bone resorption, which method comprises administering to a subject in need of such treatment a bone resorption inhibitory effective amount of a compound comprising at least amino acids 107-111 of the carboxyl terminus of PTHrP or a derivative thereof, optionally in association with at least one pharmaceutically acceptable carrier or excipient.

In accordance with a further aspect of this invention, there is provided a method for the treatment of diseases characterised by excess bone resorption, including osteoporosis, Paget's disease of bone, humoral hypercalcemia of malignancy, and metastic bone diseases, which method comprises administering to a subject in need of such treatment a bone resorption inhibitory effective amount of a compound comprising at least amino acids 107-111 of the carboxyl terminal fragment of PTHrP or a derivative thereof, optionally in association with a pharmaceutically acceptable carrier or excipient.

The dose, carrier, frequency and route of administration of carboxyl terminal fragments of PTHrP to a patient, will depend, among other factors, on the condition of the patient, the target disorder, the desired route of administration and the activity of the carbonyl terminal fragment(s). This is readily determined and monitored by the physician during the course of the therapy.

By way of example only, a bone resorption inhibitory effective amount of carboxyl terminal fragments of PTHrP may comprise from 0.01 µg to 1 gram or more. Dosage units of carboxy terminal fragments of PTHrP may comprise about 0.05 µg to 10 mg, preferably 1 µg to 500 µg; and more preferably 10 µg to 50 µg of the active agent. Again by way of example only, a bone resorption inhibitory effective amount of PTHrP may comprise 0.001 µg of PTMP per kg of body weight to 1 mg per kg of body weight.

Carboxyl terminal fragments of PTHrP may be administered to patients by injection, such as by intravenous, intramuscular, sub-cutaneous or intratumour injection. Alternatively administration may be by infusion using intranasal, subcutaneous, intravenous, intraperitoneal or other like routes. Further administration may be by way of oral, rectal, transdermal or other conventional routes of administration well known in the art for the delivery of pharmacologically active compounds.

Various aspects of the present invention will now be exemplified, by way of non-limiting example only in the accompanying Figures and Examples.

In the Figures:

FIG. 1 shows the amino acid sequence of prepro-PTHrP;

FIG. 2 shows the effects of PTHrP (SEQ ID NO:1) peptides 1-141 (control), 107-132, 107-139, 154-173, 129-139, and chicken PTHrP (107-139) on bone resorption, measured as pit number/osteoclast (OC) number. Peptides were used a concentration of 1 nM;

FIG. 3 is essentially the same as FIG. 1 and shows the effect of varying concentrations of PTHrP (107-111) on bone resorption compared to control (PTHrP 1-141) and PTHrP 107-139; and FIG. 4 shows a dose response diagram for various peptides where resorption pits/osteoclast treated/control ratio is plotted against log[peptide] molar concentration.

EXAMPLE 1

Osteoclast Isolation and Assay of Bone Resorption

Osteoclasts were isolated from neonatal female Wistar rats by curetting the long bones into culture medium (HEPES-buffered Medium 199 [Trademark Flow Laboratories]). The resulting cell suspension was allowed to settle onto 100 µm thick slices of devitalized bovine cortical bone for 20 minutes before rinsing. After this brief settling period, the majority of contaminating cells are removed in the rinsing step, resulting in a functionally pure population of osteoclasts. The bone slices were then incubated in tissue culture medium (Eagle's Minimum Essential Medium [Flow Laboratories] supplemented, with 100 iU/ml benzylpenicillin 100 µg/ml streptomycin and 10% heat-inactivated fetal bovine serum) at 37° C. in 95% air, 5% $CO_2$, pH 7.3 in the presence or absence of test agents. After 24 hours, the cells were fixed, reacted cytochemically for tartrate-resistant acid phosphatase (TRACP) and the number of multinucleated cells with strong reactions for TRACP (i.e. osteoclasts) counted. The cells were then stripped by ultrasonication in 0.25M $NH_4OH$ prior to processing for scanning electronic microscopy. The entire surface of each bone slice was scanned and the number of resorption pits counted. In selected experiments the depth of the pits are assessed. There was a minimum of 6 replicates for each concentration point for each peptide. Each experiment was repeated at least 3 times. Statistical significance was determined by using Student's t test to compare each treatment with control. Bone resorption can be expressed as pit No./OC/ bone slice, total excavated plan area/OC/bone slice, or total excavated volume of bone/OC/bone slice. Such assays are routine and readily amenable to the screening of large numbers of compounds for bone resorption inhibitory activity.

EXAMPLE 2

Peptide Preparation and Purification

Recombinant hPTHrP(1-141) and recombinant hPTHrP (1-108) were prepared and purified as previously described (Suva et al., Supra, incorporated herein by reference). hPTHrP(107-139), Thr Arg Ser Ala Trp Leu Asp Ser Gly Val Thr Gly Ser Gly Leu Glu Gly Asp His Leu Ser Asp Thr Ser Thr Thr Ser Leu Glu Leu Asp Ser Arg-COOH (SEQ ID NO:2), and other peptides were synthesized as carboxy-terminal amides, using an Applied Biosystems Peptide Synthesizer Model 430. Following HF cleavage, peptides were extracted from the resin with 60% (v/v) acetonitrile and 0.1% (v/v) trifluoroacetic acid and lyophilized. The crude peptides were purified by ion exchange chromatography (2.5×90 cm column, C18, 20-30 µm. 300 Å resin. Vydac, California) with an acetonitrile gradient in the presence of 0.1% trifluoroacetic acid. The composition of the synthetic peptides was verified by quantitative amino acid analysis using a Beckman 6300 amino acid analyser. Cyclic AMP Assay: Osteoclasts were isolated as described above into 12-well tissue culture plates (Linbro). The cultures were pretreated with isobutylmethylxanthine (1 mM) for 20 minutes prior to administration of test peptides for 10 minutes. Cyclic AMP was extracted with 95% (v/v) ethanol/1 mM HCl and measured by radioimmunoassay. Four to six replicate wells were used in each treatment group.

EXAMPLE 3

Peptides corresponding to the carboxy terminal sequence of PTHrP were synthesized as follows:

PTHrP(107-141)
PTHrP(107-132)
PTHrP(107-119)
PTHrP(107-111)
PTHrP(129-141)
PTHrP(129-139)
PTHrP(154-173)—sequence based on alternative splicing of PTHrP
PTHrP(1-141) chicken PTHrP(107-139)

These peptides were synthesized by solid phase technology on an Applied Biosystems Synthesizer, and purified by ion exchange chromatography and reversed phase. HPLC. Amino acid content of peptides were determined after hydrolysis, using a Beckman Amino Acid Analyzer.

The above peptides were synthesized to determine the portion of the carboxy terminal region of PTHrP which is responsible for osteoclastic bone resorption. Whereas human PTHrP(107-139) and (107-132), and chicken PTHrP (107-139) produce substantial inhibition of resorption determined according to Example 1, no effect is obtained with PTHrP(129-139), or PTHrP(154-173) (control), as is evident from FIG. 2.

FIG. 3 shows that the peptide PTHrP(107-111) is a potent inhibitor of osteoclastic bone resorption at $10^{-9}$ to $10^{-15}$M. PTHrP(107-139) has like activity as does PTHrP(107-119) (data not shown).

The signal transduction mechanisms operating for PTHrP (107-139) appear to be distinct from those for calcitonin. There was no elevation of cyclic AMP in response to PTHrP(107-139) compared to a 2.5 fold response to calmon calcitonin.

The effect of PTHrP(107-139); on osteoclasts can be blocked by the protein kinase C inhibitor H7 (1-(5-isoquinolinesulfonyl)-2 methyl piperazine.

It is clear from this example that bone resorption inhibitory activity resides with PTHrP (107-111). Carboxy terminal fragments of PTHrP containing this sequence are also active in inhibiting bone resorption. Accordingly, any carboxy terminal fragment of PTHrP which contains amino acids 107-111 is active in inhibiting osteoclastic bone resorption.

EXAMPLE 4

Effective Amino Terminal Truncations and Extensions

Amino terminal truncations and extensions to the sequence PTHrP (107-111) were investigated.

Compounds were synthesized according to the methods of Example 3 and assayed for bone resorption inhibitory activity according to the methods of Example 1. Results are set forth in Table 2. Amino acids are represented using the standard single letter amino acid code and bone resorption inhibitory activity is designated by a "+" and inactivity by "−".

TABLE 2

| Sequence | Activity |
| --- | --- |
| T R S A W (SEQ ID NO: 3) | + |
| S A W amino acid 139 (PTHrP[109–139]) | − |
| R T R S A W (SEQ ID NO: 4) | +* |
| $_D$R T R S A W | − |
| Pro T R S A W (SEQ ID NO: 5) | − |

*The bone resorption inhibitory activity of the derivative RTRSAW (SEQ ID NO: 4) was approximately 10% of that of TRSAW (SEQ ID NO: 3) and other derivatives.

The peptide PTHrP (109-139) was not active, and neither was the peptide PTHrP (108-139) data not shown. This clearly evidences that amino acids 107-111 of PTHrP are required for bone resorption inhibitory activity.

The criticality of a free N-terminus at amino acid 107 was investigated by the addition of an R group (arginine) to the peptide TRSAW (SEQ ID NO:3). R is the amino acid found at position 106 of PTHrP. This peptide showed approximately 10% of the activity of PTHrP (107-111). It may be postulated from this result that a free N-terminus is not required at amino acid 107 of the carboxy terminal fragment of PTHrP, or rather that amino acid 106 in the peptide PTHrP (106-111) was cleaved to give PTHrP (107-111).

To investigate the above alternatives, R in the D-amino acid form was added to the peptide TRSAW (SEQ ID NO:3) to give $_D$RTRSAW. D-amino acids are not capable of proteolytic cleavage by proteolytic enzymes. Accordingly, if PTHrP (106-111) is active by virtue of cleavage of amino acid 106 to yield the free amino terminus at amino acid 107, a derivative having a D-amino acid, specifically $_D$R would be expected to be inactive. If there is no requirement for a free N-amino terminus at amine acid 107 of the carboxy terminal fragments of PTHrP, and further that the nature of the amine acid at position 106 is not important, then the derivative $_D$RTRSAW would be expected to be active. The results presented above show that the addition of a D-amino acid which corresponds to amino acid 106 of PTHrP destroys activity of the TRSAW (SEQ ID NO: 3) peptide. Hence, a free N-terminal at amino acid 107 is required. If a protecting group is not cleavable from amino acid 107 of a PTHrP carboxyl fragment or a derivative thereof the bone resorption inhibitory activity is lost.

Further support for this view is evidenced by the peptide PTRSAW (SEQ ID NO: 5). The amino acid proline as represented by the designation P is not generally clearable by proteolytic enzymes from a peptide chain. As expected, the presence of proline as amino acid 106 of the carboxyl terminal fragment of PTHrP destroys activity.

As the peptide RTRSAW (SEQ ID NO:4) corresponding to PTHrP (106-111) possesses bone resorption inhibitory activity, it is clear that a hydrolysable group may be added to the amino terminus of amino acid 107 and derivatives thereof. Experiments involving the addition of trifluoroacetic acid (TFA) to the N-terminal of amino acid 107 also show that such derivatives show bone resorption inhibitory activity (data not shown) this clearly being due to the removal of TFA from the amino terminus.

EXAMPLE 5

Amine acid derivatives of PTHrP (107-111) were prepared and assayed for bone resorption inhibition according to Example 4, to investigate the relative plasticity of the active site of carboxy terminal fragments of PTHrP, namely PTHrP (107-111). Results are shown in Table 3.

TABLE 3

| Effect of Amino Acid Substitutions | |
| --- | --- |
| Sequence | Activity |
| T R S A W (SEQ ID NO: 3) | + |
| succ T R S A W (SEQ ID NO: 6) | − |
| P R S A W (SEQ ID NO: 7) | + |
| A R S A W (SEQ ID NO: 8) | + |
| T K S A W (SEQ ID NO: 9) | + |
| T R A A W (SEQ ID NO: 10) | + |
| A R A A W (SEQ ID NO: 11) | + |
| T R SmeA W (SEQ ID NO: 12) | + |
| T R S A Y (SEQ ID NO: 13) | + |
| T R S A$\phi$G (SEQ ID NO: 14) | + |
| T R C A W P G T C (SEQ ID NO: 15) | + |
| T H S A W (SEQ ID NO: 16) | + |
| T R S npA (SEQ ID NO: 17) | + |
| S R T A W (SEQ ID NO: 18) | − |
| $_D$W$_D$A$_D$S$_D$R$_D$T | + | where npA is 3(2-napthyl)alanine

φG is α-phenyl glycine me is α-methyl

Succ is N-succinyl-

"D" refers to D-amino acid isomer

It is clear from the above results that amino acids 107-111 of PTHrP tolerate significant variation, that is amino acid substitutions may be made without loss of activity.

Amino acid 107 represented by T in the sequence TRSAW (SEQ ID NO:3) (corresponding to PTHrP 107-111) may be any residue of an amino acid. In this Examples amino acid 107 is variously Thr, Ala, Pro, Ser, meSer and SuccThr.

Surprisingly, the retroinverted-sequence $_DW_DA_DS_DR_DT$ was found to be active in inhibiting bone resorption. It is believed that the retroinverted conformation of this peptide is sufficiently similar in side chain orientation to the sequence TRSAW (SEQ ID NO:3) so as to mimic activity.

Table 4 depicts the effects of peptide length and amino acid composition on the ability of PTHrP to inhibit bone resorption by isolated osteoclasts.

TABLE 4

| ACTIVE PEPTIDES | | | | | | $EC_{50}$* | INACTIVE PEPTIDES∞ | | | | | |
|---|---|---|---|---|---|---|---|---|---|---|---|---|
| PTHrP[1–141] | | | | | | $10^{-11}$M | PTHrP[1–34] | | | | | |
| PTHrP[107–139] | | | | | | $10^{-15}$M | PRHrP[1–108] | | | | | |
| | | | | | | | PTHrP[109–139] | | | | | |
| T | R | S | A | W | (SEQ ID NO: 3) § | $10^{-15}$M | | | | | | |
| A | R | S | A | W | (SEQ ID NO: 8) ¶ | $10^{-15}$M | | | | | | |
| | | | | | | | AcT | R | S | A | W | (SEQ ID NO: 21) |
| P | R | S | A | W | (SEQ ID NO: 7) ‡ | | SucT | R | S | A | W | (SEQ ID NO: 6) |
| meA | R | S | A | W | (SEQ ID NO: 19) | | Y | R | S | A | W | (SEQ ID NO: 22) |
| | | | | | | | T | $_DR$ | S | A | W | |
| T | K | S | A | W | (SEQ ID NO: 9) | $10^{-15}$M | T | A | S | A | W | (SEQ ID NO: 23) |
| T | H | S | A | W | (SEQ ID NO: 16) | $10^{-15}$M | T | R | S | P | W | (SEQ ID NO: 24) |
| T | R | A | A | W | (SEQ ID NO: 10) | $10^{-15}$M | | | | | | |
| A | R | A | A | W | (SEQ ID NO: 11) | $10^{-14}$M | T | R | S | A | clF | |
| T | R | C | A | W | PGTC (SEQ ID NO: 15) | $10^{-15}$M | T | R | S | A | $_DW$ | (SEQ ID NO: 25) |
| | | | | | | | $_DR$ T | R | S | A | W | |
| T | R | S | meA | W | (SEQ ID NO: 12) | $10^{-15}$M | | S | S | A | W | |
| T | R | S | A | Y | (SEQ ID NO: 13) | $10^{-15}$M | S | R | T | A | W | (SEQ ID NO: 18) |
| T | R | S | A | phG | (SEQ ID NO: 14) | | W | A | S | R | T | (SEQ ID NO: 26) |
| T | R | S | A | napA | (SEQ ID NO: 20) | | | | | | | |
| R T | R | S | A | W | (SEQ ID NO: 4) | $10^{-14}$M | | | | | | |
| $_DW$ $_DA$ $_DS$ $_DR$ $_DT$ | | | | | | $10^{-9}$M | | | | | | |

Abbreviations: Ac: N-acetyl-, Suc: N-succinyl-, meA: αmethyl alanine, phG: αphenylglycine, napA: 3(2-naphthyl)alanine, clF: parachloro-L-phenylalanine

*$EC_{50}$'s (active peptides only) were calculated from at least 2 dose-response curves testing concentrations between $10^{-16}$M and $10^{-7}$M.

∞ No inhibition of bone resorption seen at $10^{-9}$M or $10^{-14}$M.

§ native human, rat and mouse PTHrP[107–111].

¶ native chicken PTHrP[107–111].

‡ $EC_{50}$ not calculated but peptide equally effective as TRSAW (SEQ ID NO: 3) at $10^{-14}$M and $10^{-9}$M.

Boxed regions indicate residues homologous with native mammalian and chicken PTHrP.

Amino acid 108, represented by R in the sequence TRSAW (SEQ ID NO:3), is generally a basic residue of an amino acid. As specifically shown in this example, amino acid 108 may be Arg, Lys, His and D-Ala.

Amino acid 109 represented by S in the sequence TRSAW (SEQ ID NO:3) may be a non-polar or uncharged polar residue of an amino acid. As specifically shown in this Example, amino acid 109 is Ser, Ala, Gly, Cys, Tyr and D-Ser.

Amino acid 110 represented by A in the sequence TRSAW (SEQ ID NO:3) may also be a non-polar or uncharged polar residue of an amino acid. As specifically exemplified in this example, amino acid 110 may also be Ala, MeAla, 3-(2napthyl)-alanine and D-Arg.

Amino acid 111 of the carboxy terminal fragment of PTHrP is generally an aromatic amino acid. Amino acid substitutions include Tyr, α-phenylglycine and α-napthylanine.

These specific amino acid variants are not be construed as any way limiting on the invention described herein. Peptides containing amino acid variants and modification can be readily tested according to Example 1 to determine whether various derivatives of carboxy terminal fragments of PTHrP possess bone resorption inhibitory activity.

Carboxy terminal extensions beyond amino acid 111 do not adversely effect activity.

FIG. 4 shows a dose response diagram for the peptides TRSAW (SEQ ID NO: 3), RTRSAW (SEQ ID NO:1), $_DW_DA_DS_DR_DT$ and $_DRTRSAW$ where resorption pits/osteoclast treated/control ratio is plotted against log molar concentration of peptide. TRSAW (SEQ ID NO:3) is the most active peptide, $_DW_DA_DS_DR_DT$ the least active.

EXAMPLE 6

In vivo activity of compound of this invention were tested in rats, as a model for mammalian therapy.

Mammalian serum calcium levels are tightly controlled by homeostatic mechanisms and show little variation. A model peptide, PTHrP 107-139 was injected intraveneously into rats (n=10) in an amount of 100 nanograms 100 grams body weight whereafter serum calcium levels were measured at 30 and 60 minutes by atomic absorption spectrascopy according to standard methods. Control groups of animals were injected with a positive control, calcitonin, which causes a decrease in serum calcium levels, as well as a negative control in the form of saline. Two groups of 10 rats ware used in these controls.

In control rats injected with normal saline, serum calcium levels were about 2.58 millimolar at 30 and minutes after injection. It is believed this level reflects normal serum calcium levels. For animals injected with PTHrP 107-139 the average serum calcium level at 30 minutes after injection was 2.35 millimolar. This reflects a significant reduction in serum calcium levels resulting from blockage or inhibition of bone resorption, with attendant bone remodelling. At 60 minutes after injection, rats injected with PTHrP 107-139 had serum calcium levels of about 2.55 millimolar. This data indicates that PTHrP 107-139 causes a transient decrease in serum calcium levels with normalisation of serum calcium levels being achieved about 30 minutes after injection of PTHrP 107-139.

When calcitonin was administered to rats in an amount of 100 nanograms 100 grams body weight, similar results were seen as for PTHrP 107-139, that is a transient reduction in serum calcium, with a reduction over 30 minutes of serum calcium to about 2.35 millimolar.

PTHrP 107-139 is representative of compounds within the scope, of this invention. Peptides containing the 107-111 epitope would be expected, on the basis of in-vitro bone resorption inhibitory data to exhibit the same in-vivo effects as PTHrP 107-139.

The direct inhibitory actions of PTHrP 107-111 compared to the indirect stimulatory actions of PTHrP 1-34 on osteoclast bone resorption in-vivo is set out in Scheme A.

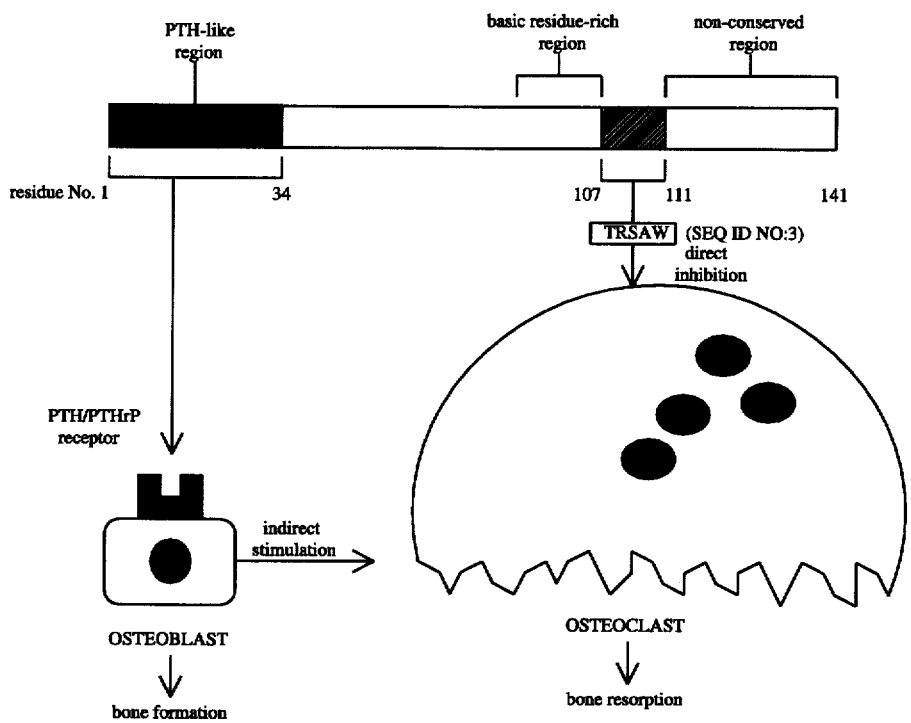

Those skilled in the art will appreciate that the invention described herein is susceptible to variations and modifications other than those specifically described. It is to be understood that the invention includes all such variations and modifications which fall within its spirit and scope. The invention also includes all of the steps, features, compositions and compounds referred to or indicated in this specification, individually or collectively, and any and all combinations of any two or more of said steps or features.

What is claimed is:

1. A polypeptide having bone resorption inhibitory activity, said polypeptide having an amino acid sequence:

$$Xaa_1\text{-}Xaa_2\text{-}Xaa_3\text{-}Xaa_4\text{-}Xaa_5\text{-}Z,$$

wherein:

Xaa$_1$ is an amino acid selected from the group consisting of Thr, Ala, Cys, Pro, D-Trp and n-methylalanine;

Xaa$_2$ is an amino acid selected from the group consisting of Arg, Lys, His, and D-Ala;

Xaa$_3$ is an amino acid selected from the group consisting of Ser, Ala, Cys, and D-Ser;

Xaa$_4$ is an amino acid selected from the group consisting of Ala, n-methylalanine, (3-(2-napthyl)-alanine), and D-Arg;

Xaa$_5$ is an amino acid selected from the group consisting of Tyr, Trp, D-Thr, α-phenylglycine, and α-napthylalanine;

Z is present or absent, and when present consists of an amino acid sequence beginning at PTHrP amino acid residue 112 as shown in FIG. 1 (SEQ ID NO:1) and ending at any PTHrP amino acid from 112 to 173 as shown in FIG. 1 (SEQ ID NO:1);

or wherein Xaa$_1$-Xaa$_2$-Xaa$_3$-Xaa$_4$-Xaa$_5$-Z is the sequence RTRSAW (SEQ ID NO:4) or TRCAWPGTC (SEQ ID NO:15), and where "D" refers to the D-amino acid isomer;

excluding PTHrP(107-138) and PTHrP(107-141).

2. The polypeptide according to claim 1 wherein the amino acid sequence Xaa$_1$-Xaa$_2$-Xaa$_3$-Xaa$_4$-Xaa$_5$ consists of amino acids 107-111 of the parathyroid hormone related protein (PTHrP) shown in FIG. 1 (SEQ ID NO:1).

3. The polypeptide according to claim 2, wherein the polypeptide is a fragment of the PTHrP shown in FIG. 1 (SEQ ID NO:1), wherein the fragment is selected from the group consisting of:
PTHrP (107-111)
PTHrP (107-112)
PTHrP (107-113)
PTHrP (107-114)
PTHrP (107-115)
PTHrP (107-116)
PTHrP (107-117)
PTHrP (107-118)
PTHrP (107-119)
PTHrP (107-120)
PTHrP (107-121)
PTHrP (107-122)
PTHrP (107-123)
PTHrP (107-124)
PTHrP (107-125)
PTHrP (107-126)
PTHrP (107-127)
PTHrP (107-128)
PTHrP (107-129)
PTHrP (107-130)
PTHrP (107-131)
PTHrP (107-132)
PTHrP (107-133)
PTHrP (107-134)
PTHrP (107-135)
PTHrP (107-136)
PTHrP (107-137)
PTHrP (107-139)
PTHrP (107-140)
PTHrP (107-142)
PTHrP (107-143)
PTHrP (107-144)
PTHrP (107-145)
PTHrP (107-146)
PTHrP (107-147)
PTHrP (107-148)
PTHrP (107-149)
PTHrP (107-150)
PTHrP (107-151)
PTHrP (107-152)
PTHrP (107-153)
PTHrP (107-154)
PTHrP (107-155)
PTHrP (107-156)
PTHrP (107-157)
PTHrP (107-158)
PTHrP (107-159)
PTHrP (107-160)
PTHrP (107-161)
PTHrP (107-162)
PTHrP (107-163)
PTHrP (107-164)
PTHrP (107-165)
PTHrP (107-166)
PTHrP (107-167)
PTHrP (107-168)
PTHrP (107-169)
PTHrP (107-170)
PTHrP (107-171)
PTHrP (107-172) and;
PTHrP (107-173).

4. The polypeptide according to claim 2 or 3 wherein the amino terminus of amino acid 107 of PTHrP is protected with a hydrolyzable protecting group.

5. The polypeptide according to claim 1 wherein the amino acid residue Xaa$_1$ is protected with a hydrolyzable protecting group.

6. The polypeptide according to claim 1 selected from the group consisting of:
T R S A W (SEQ ID NO:3)
A R S A W (SEQ ID NO:8)
meA R S A W (SEQ ID NO:19)
R T R S A W (SEQ ID NO:4)
T R S A Y (SEQ ID NO:13)
T R A A W (SEQ ID NO:10)
A R A A W (SEQ ID NO:11)
$_DW_DA_DS_DR_DT$
T R C A W P G T C (SEQ ID NO:15)
P R S A W (SEQ ID NO:7)
T K S A W (SEQ ID NO:9)

T R S meA W (SEQ ID NO:12)
T R S A ϕG (SEQ ID NO:14)
T H S A W (SEQ ID NO:16) and
T R S A npA, (SEQ ID NO:20)
where "D" refers to the D-amino acid isomer;
ϕG is α-phenylglycine;
meA is n-methylalanine;
npA is 3(2-napthyl)alanine.

7. A composition which comprises the polypeptide according to claim 1 in association with one or more pharmaceutically acceptable carriers or excipients.

8. A method for the inhibition of bone resorption in a subject, which method comprises administering a bone resorption inhibitory amount of the polypeptide as claimed in claim 1, optionally in association with at least one pharmaceutically acceptable carrier or excipient.

9. The method according to claim 8 wherein said polypeptide is a fragment of the PTHrP shown in FIG. 1 (SEQ ID NO:1), wherein the fragment is selected from the group consisting of:
PTHrP (107-111)
PTHrP (107-112)
PTHrP (107-113)
PTHrP (107-114)
PTHrP (107-115)
PTHrP (107-116)
PTHrP (107-117)
PTHrP (107-118)
PTHrP (107-119)
PTHrP (107-120)
PTHrP (107-121)
PTHrP (107-122)
PTHrP (107-123)
PTHrP (107-124)
PTHrP (107-125)
PTHrP (107-126)
PTHrP (107-127)
PTHrP (107-128)
PTHrP (107-129)
PTHrP (107-130)
PTHrP (107-131)
PTHrP (107-132)
PTHrP (107-133)
PTHrP (107-134)
PTHrP (107-135)
PTHrP (107-136)
PTHrP (107-137)
PTHrP (107-139)
PTHrP (107-140)
PTHrP (107-142)
PTHrP (107-143)
PTHrP (107-144)
PTHrP (107-145)
PTHrP (107-146)
PTHrP (107-147)
PTHrP (107-148)
PTHrP (107-149)
PTHrP (107-150)
PTHrP (107-151)
PTHrP (107-152)
PTHrP (107-153)
PTHrP (107-154)
PTHrP (107-155)
PTHrP (107-156)
PTHrP (107-157)
PTHrP (107-158)
PTHrP (107-159)
PTHrP (107-160)
PTHrP (107-161)
PTHrP (107-162)
PTHrP (107-163)
PTHrP (107-164)
PTHrP (107-165)
PTHrP (107-166)
PTHrP (107-167)
PTHrP (107-168)
PTHrP (107-169)
PTHrP (107-170)
PTHrP (107-171)
PTHrP (107-172) and;
PTHrP (107-173).

10. The method according to claim 8 wherein the amino acid sequence $Xaa_1$-$Xaa_2$-$Xaa_3$-$Xaa_4$-$Xaa_5$ consists of amino acids 107-111 of the parathyroid hormone related protein (PTHrP) shown in FIG. 1 (SEQ ID NO:1).

11. The method according to claim 8 wherein said polypeptide is selected from the group consisting of:
T R S A W (SEQ ID NO:3)
A R S A W (SEQ ID NO:8)
meA R S A W (SEQ ID NO:19)
R T R S A W (SEQ ID NO:4)
T R S A Y (SEQ ID NO:13)
T R A A W (SEQ ID NO:10)
A R A A W L (SEQ ID NO:11)
$_DW_DA_DS_DR_DT$
T R C A W P G T C (SEQ ID NO:15)
P R S A W (SEQ ID NO:7)
T K S A W (SEQ ID NO:9)
T R S meA W (SEQ ID NO:12)
T R S A ϕG (SEQ ID NO:14)
T H S A W (SEQ ID NO:16) and
T R S A npA, (SEQ ID NO:20)
where "D" refers to the D-amino acid isomer;
ϕG is α-phenylglycine;
meA is n-methylalanine;
npA is 3(2-napthyl)alanine.

12. A method according to claim 8 which is a method for the amelioration of bone resorption associated with zero gravity.

13. The method according to any of claims 9–11 wherein the amino terminal amino acid is protected with a hydrolyzable protecting group.

14. A method for the treatment of diseases characterized by excess bone resorption which method comprises administering to a subject in need of such treatment a bone resorption inhibitory amount of the polypeptide according to claim 1, optionally in association with a pharmaceutically acceptable carrier or excipient.

15. The method according to claim 14 wherein said polypeptide is a fragment of the PTHrP shown in FIG. 1 (SEQ ID NO:1), wherein the fragment is selected from the group consisting of:
PTHrP (107-111)
PTHrP (107-112)
PTHrP (107-113)
PTHrP (107-114)
PTHrP (107-115)
PTHrP (107-116)
PTHrP (107-117)
PTHrP (107-118)
PTHrP (107-119)
PTHrP (107-120)
PTHrP (107-121)
PTHrP (107-122)

PTHrP (107-123)
PTHrP (107-124)
PTHrP (107-125)
PTHrP (107-126)
PTHrP (107-127)
PTHrP (107-128)
PTHrP (107-129)
PTHrP (107-130)
PTHrP (107-131)
PTHrP (107-132)
PTHrP (107-133)
PTHrP (107-134)
PTHrP (107-135)
PTHrP (107-136)
PTHrP (107-137)
PTHrP (107-139)
PTHrP (107-140)
PTHrP (107-142)
PTHrP (107-143)
PTHrP (107-144)
PTHrP (107-145)
PTHrP (107-146)
PTHrP (107-147)
PTHrP (107-148)
PTHrP (107-149)
PTHrP (107-150)
PTHrP (107-151)
PTHrP (107-152)
PTHrP (107-153)
PTHrP (107-154)
PTHrP (107-155)
PTHrP (107-156)
PTHrP (107-157)
PTHrP (107-158)
PTHrP (107-159)
PTHrP (107-160)
PTHrP (107-161)
PTHrP (107-162)
PTHrP (107-163)
PTHrP (107-164)
PTHrP (107-165)
PTHrP (107-166)
PTHrP (107-167)
PTHrP (107-168)
PTHrP (107-169)
PTHrP (107-170)
PTHrP (107-171)
PTHrP (107-172) and;
PTHrP (107-173).

16. The method according to claim 14 wherein the amino acid sequence $Xaa_1$-$Xaa_2$-$Xaa_3$-$Xaa_4$-$Xaa_5$ consists of amino acids 107-111 of the parathyroid hormone related protein (PTHrP) shown in FIG. 1 (SEQ ID NO:1).

17. A method according to claim 14 wherein said polypeptide is selected from the group consisting of:
T R S A W (SEQ ID NO:3)
A R S A W (SEQ ID NO:8)
meA R S A W (SEQ ID NO:19)
R T R S A W (SEQ ID NO:4)
T R S A Y (SEQ ID NO:13)
T R A A W (SEQ ID NO:10)
A R A A W (SEQ ID NO:11)
$_DW_DA_DS_DR_DT$
T R C A W P G T C (SEQ ID NO:15)
P R S A W (SEQ ID NO:7)
T K S A W (SEQ ID NO:9)
T R S meA W (SEQ ID NO:12)
T R S A φG (SEQ ID NO:14)
T H S A W (SEQ ID NO:16) and
T R S A npA, (SEQ ID NO:20)
where "D" refers to the D-amino acid isomer;
φG is α-phenylglycine;
meA is n-methylalanine;
npA is 3(2-napthyl)alanine.

18. A method according to claim 14 wherein said diseases are selected from the group consisting of osteoporosis, Paget's disease of bone, humoral hypercalcemia of malignancy and metastic bone diseases.

19. The method according to any of claims 15–17 wherein the amino terminal amino acid is protected with a hydrolyzable protecting group.

* * * * *